US011246333B2

(12) United States Patent
Mitchell et al.

(10) Patent No.: US 11,246,333 B2
(45) Date of Patent: Feb. 15, 2022

(54) PRODUCE ORIENTOR (71) Applicant: Atlas Pacific Engineering Company, Pueblo, CO (US)

(72) Inventors: Russ Mitchell, San Diego, CA (US); Brandon Evers, San Diego, CA (US); Brian Dunne, Poway, CA (US); Daniel Nelson, El Cajon, CA (US); Mason McInnis, Granite Bay, CA (US); David Bullock, Pueblo, CO (US)

(73) Assignee: Atlas Pacific Engineering Company, Pueblo, CO (US)

( * ) Notice: Subject to any disclaimer, the term of this patent is extended or adjusted under 35 U.S.C. 154(b) by 43 days.

(21) Appl. No.: 16/501,231

(22) Filed: Mar. 8, 2019

(65) Prior Publication Data
US 2019/0281879 A1  Sep. 19, 2019

Related U.S. Application Data (60) Provisional application No. 62/761,243, filed on Mar. 14, 2018.

(51) Int. Cl.
*G06K 9/00* (2006.01)
*A23N 4/14* (2006.01)
(Continued)

(52) U.S. Cl.
CPC ............. *A23N 4/14* (2013.01); *A23N 7/02* (2013.01); *B25J 11/0045* (2013.01);
(Continued)

(58) Field of Classification Search
None
See application file for complete search history.

(56) References Cited

U.S. PATENT DOCUMENTS 3,586,081 A * 6/1971 Loveland .............. A23N 7/026
99/542
3,586,151 A * 6/1971 Loveland ................ A23N 4/14
198/385
(Continued)

FOREIGN PATENT DOCUMENTS

CN  101425187 A * 5/2009

OTHER PUBLICATIONS

Pfaff et al., "Application of Fin Ray effect approach for production process automation." Annals of DAAAM & Proceedings 22, No. 1 (2011): 1247-1249. (Year: 2011).*
(Continued)

*Primary Examiner* — Feng Niu
(74) *Attorney, Agent, or Firm* — Jones Day (57) ABSTRACT A method of automatically orienting symmetric and asymmetric produce items, such as apples for example, is provided. Individual items of produce are manipulated by a programmable manipulator within the view of one or more depth imaging cameras. Digital three dimensional characterizations of the surface of the produce items are generated by the depth imaging camera or cameras and are utilized by a computer connected to the depth imaging camera or cameras to locate the stem and blossom of each produce item. Asymmetric produce items, such as apples with dropped shoulders as well as symmetric produce items can be properly oriented and processed automatically.

17 Claims, 11 Drawing Sheets (51) Int. Cl.
*G01N 33/02* (2006.01)
*B25J 11/00* (2006.01)
*A23N 7/02* (2006.01)
*G06T 7/55* (2017.01)
*H04N 5/247* (2006.01)
*G06T 7/90* (2017.01)
*G06T 7/73* (2017.01)

(52) U.S. Cl.
CPC .............. *G01N 33/025* (2013.01); *G06T 7/55* (2017.01); *G06T 7/75* (2017.01); *G06T 7/90* (2017.01); *H04N 5/247* (2013.01); *G06T 2207/10024* (2013.01); *G06T 2207/10028* (2013.01); *G06T 2207/30128* (2013.01)

(56) References Cited

U.S. PATENT DOCUMENTS

| | | | | |
|---|---|---|---|---|
| 3,610,303 A | * | 10/1971 | Loveland | A23N 4/14 |
| | | | | 99/542 |
| 5,526,119 A | * | 6/1996 | Blit | B07C 5/3422 |
| | | | | 209/577 |
| 5,855,270 A | * | 1/1999 | Throop | B65G 47/24 |
| | | | | 198/394 |
| 7,133,572 B2 | * | 11/2006 | Neubauer | G06K 9/6204 |
| | | | | 382/282 |
| 7,917,342 B2 | * | 3/2011 | Miura | G06T 17/30 |
| | | | | 703/2 |
| 9,364,020 B2 | * | 6/2016 | Tao | B26F 3/004 |
| 10,373,369 B2 | * | 8/2019 | Rad | G06K 9/00208 |
| 10,379,035 B2 | * | 8/2019 | Noda | G01N 21/8851 |
| 10,755,433 B2 | * | 8/2020 | Wasik | G06T 7/579 |
| 2004/0066964 A1 | | 4/2004 | Neubauer et al. | |
| 2006/0129361 A1 | | 6/2006 | Miura et al. | |
| 2008/0101657 A1 | * | 5/2008 | Durkin | G01N 21/6456 |
| | | | | 382/110 |
| 2013/0250050 A1 | * | 9/2013 | Kanaujia | H04N 13/106 |
| | | | | 348/42 |
| 2014/0272055 A1 | * | 9/2014 | Tao | B26D 5/00 |
| | | | | 426/484 |
| 2017/0079318 A1 | | 3/2017 | Crescenzo et al. | |
| 2017/0238594 A1 | | 8/2017 | Turatti | |
| 2017/0245540 A1 | * | 8/2017 | Mclean | A23N 4/14 |
| 2017/0287162 A1 | * | 10/2017 | Wasik | G06T 7/73 |
| 2018/0180534 A1 | * | 6/2018 | Noda | G06T 7/0004 |
| 2018/0268601 A1 | * | 9/2018 | Rad | G06T 7/75 |
| 2019/0147221 A1 | * | 5/2019 | Grabner | G06T 7/75 |
| | | | | 382/103 |

OTHER PUBLICATIONS

International Search Report & Written Opinion; PCT/US19/00008; Jun. 11, 2019.

* cited by examiner

PRODUCE ORIENTOR

CROSS REFERENCE TO RELATED APPLICATION

The present application claims the benefit of and priority from U.S. provisional application Ser. No. 62/761,243 filed Mar. 14, 2018.

BACKGROUND

The present invention pertains in general to the automatic orienting of produce items, so that those items can subsequently be processed automatically by peelers, coring devices and slicers, for example. The following description and drawings will show and describe the invention primarily as utilized in automatically orienting apples. However, it is to be understood that the invention can be applied to other produce items such as peaches, pears and apricots, for example.

In the case of automatically orienting apples, the prior art has typically concentrated on locating either the stem indent, in which the stem is located, or the blossom indent, in which the blossom is located, of the apple, and then assumes that the body of the apple is symmetrical along an axis from the blossom indent to the stem indent, i.e. that the stem and blossom are vertically aligned. This assumption is valid for some apples, but not all. Many apples (5% in some varieties) are not symmetrical along an axis from the blossom to the stem. Furthermore, changes in apple varieties, cultivation practices and climate have resulted in an increase in the percentage of "dropped shoulder" apples, which are asymmetrical. When such an asymmetric apple is transferred either blossom indent or stem indent downwardly to a common automatic vertically mounted coring tube, the coring tube enters the apple at a point away from the uppermost indent and does not remove the entire core of the apple, and undesirable seeds and other core materials are not removed. That asymmetric apple cannot be used, and to make matters worse, it must be separated and disposed of. The result is the loss of the apple, the effort and expense required to detect and separate that apple, and the added expense of disposing of the remains of that apple. If an asymmetric apple is not detected and separated the undesirable seeds and core material may reduce the quality and/or usability of a large number of the processed apples The present invention, for the first time known to the applicants, provides a system for automatically locating the stem and blossom of an apple, regardless of the shape of the apple. Once the stem and blossom are automatically located, the apple is automatically manipulated to align the apple so that the automatic coring of the apple will successfully remove all of the unwanted seeds and other undesirable core material from the apple.

The present invention reduces the waste otherwise caused by using typical prior art automatic orienting apparatus, eliminates the effort and expense of locating and separating asymmetric apples and eliminates the expense of disposing of the remains of apples not successfully cored or otherwise not successfully processed.

A typical prior art apple orientor is shown in Tichy U.S. Pat. No. 4,746,001. Apples are conveyed singularly into a receptacle in which apples are rotated by wheels below the apple until either the blossom indent or stem indent loses contact with the wheels and the apple comes to rest at the base of receptacle. The apple is then assumed to be oriented and is transferred to a vertical coring machine. However, if the apple is asymmetrical about an axis extending from its blossom to its stem, it will not be successfully cored, resulting in the losses and added expense noted above.

The Ross et al U.S. Pat. No. 5,544,731 and Amstad U.S. Pat. No. 4,169,528 teach apple orientors which either agitate or rotate apples until either end of the apple comes to rest at the base of a receptacle. These devices also transfer the apple to a vertically actuated coring tube, assuming the upper end of the apple to be vertically aligned with the lower end of the apple. As noted above, the coring of asymmetric apples with these orientors is not successful.

The Throop et al U.S. Pat. No. 5,855,270 teaches an apple or other produce orienting device using a pair of opposed rollers on horizontal axes to cause the stem and blossom to be oriented on a horizontal axis. This system also does not properly orient asymmetric apples.

The prior art includes pear orienting machines described in Meissner et al U.S. Pat. No. 4,907,687; Colombo U.S. Pat. No. 4,766,990; Meissner et al U.S. Pat. No. 4,487,307, Smith U.S. Pat. No. 4,010,842 and Paterson et al U.S. Pat. No. 5,413,206 all of which use various conveying techniques to position the stem ends of pears lowermost for transfer to coring machines.

The prior art described above locates either the stem end or blossom end of the produce item and assumes the apple (or pear) is symmetrical about an axis extending from the stem to the blossom, and that the stem and blossom are vertically aligned.

What is needed in this art is a system for orienting produce items that is capable of orienting such items that are asymmetrical about an axis between the stem and blossom.

The present invention achieves that result, and avoids the expense and waste caused by asymmetric produce as described above.

BRIEF SUMMARY OF THE INVENTION

The present invention is a significant departure and improvement over the prior art. One or more depth imaging cameras are utilized together with a programmable, robotic manipulator to create a current three dimensional "characterization" of the surface of an apple (or other produce item) to be oriented. In a first embodiment, the three dimensional "characterization" is a three dimensional model of the surface of the current apple. That current model is then automatically compared with a digitally stored library of three dimensional models of properly oriented symmetric and asymmetric apples (or other produce items) to locate the closest match. The programmable manipulator is then automatically actuated to correct the orientation of the current apple.

In this first embodiment, if the current apple has a "dropped shoulder," the three dimensional model of that current apple will be compared with properly oriented "dropped shoulder" three dimensional models stored in a digital library accessible by the camera via computer to locate a match. The match model is determined using an Iterative Closest Point (ICP) algorithm. The programmable manipulator is then actuated to correct the orientation of the current apple.

In a second embodiment, preferred for use with apples, a Principal Axis of Curvature (PAC) algorithm is utilized together with a computer, programmable manipulator and one or more depth imaging cameras to create a three dimensional map of the slope for each point on the surface of the apple. The stem and blossom indents of apples have the highest cluster of high slopes, and locating those clusters locates the stem and blossom indents, and the stems and blossoms. Once the stem and blossom indents are located, the manipulator is actuated to correct the orientation of the apple. This embodiment does not require a digital library of stored three dimensional models.

For the first time known to applicants, asymmetric and symmetric apples (or other produce), can be automatically oriented to a desired position as required for subsequent automatic processing such as coring, peeling, etc.

Another aspect of the invention is that bruised apples (or other produce) unacceptable for processing can be identified and separated by the use of color sensitive depth imaging cameras.

A primary object of the invention is to provide a method for automatically orienting asymmetrical, as well as symmetrical, apples and other produce items such a peaches, pears and apricots for further processing such as coring, peeling or pit removal (in the case of peaches and apricots).

A further object of the invention is to reduce the amount of waste, and the expense in dealing with waste occurring in the automatic processing of apples and other produce.

Another object is to increase the yield in the automatic processing of apples and other produce.

A further object is to provide an automatic method of locating and separating bruised apples unfit for processing before any processing has begun.

These and other objects and advantages will become apparent from the description below and the drawings.

DETAILED DESCRIPTION OF THE DRAWINGS

Figure 1:
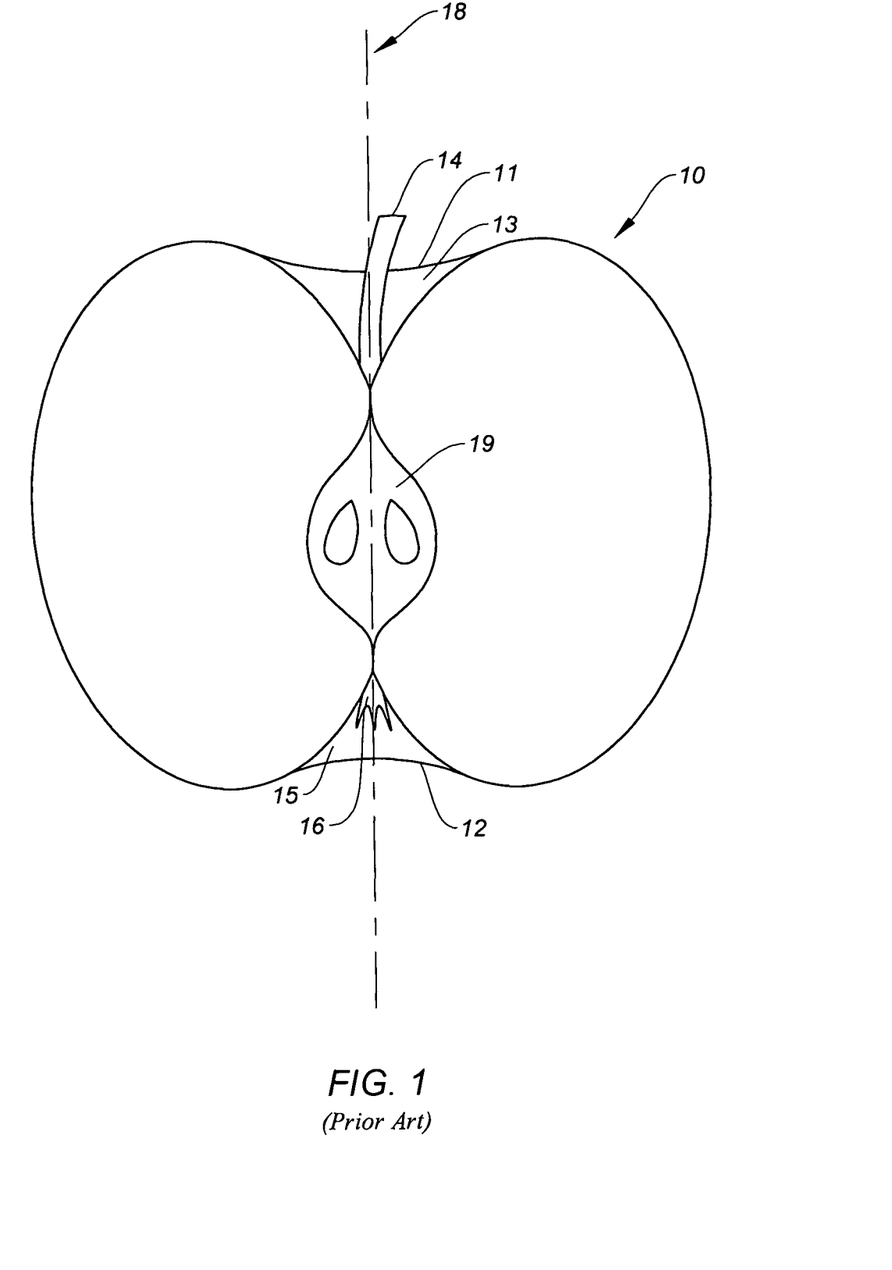
FIG. 1 is a schematic cross-sectional illustration of a symmetrical apple.

FIG. 1 is a schematic cross-sectional representation of a symmetrical apple 10 having a stem 14 at upper end 11 with stem indent 13 and a blossom end 12 with blossom indent 15 and blossom 16. The upper indent 13 contains stem 14. The blossom indent 15 contains blossom 16. Axis 18 extends vertically from stem 14 to blossom 16 and is the correct axis along which coring tubes move to remove the undesirable seed cell 19. Apple 10 is symmetrical relative to axis 18.

Figure 2:
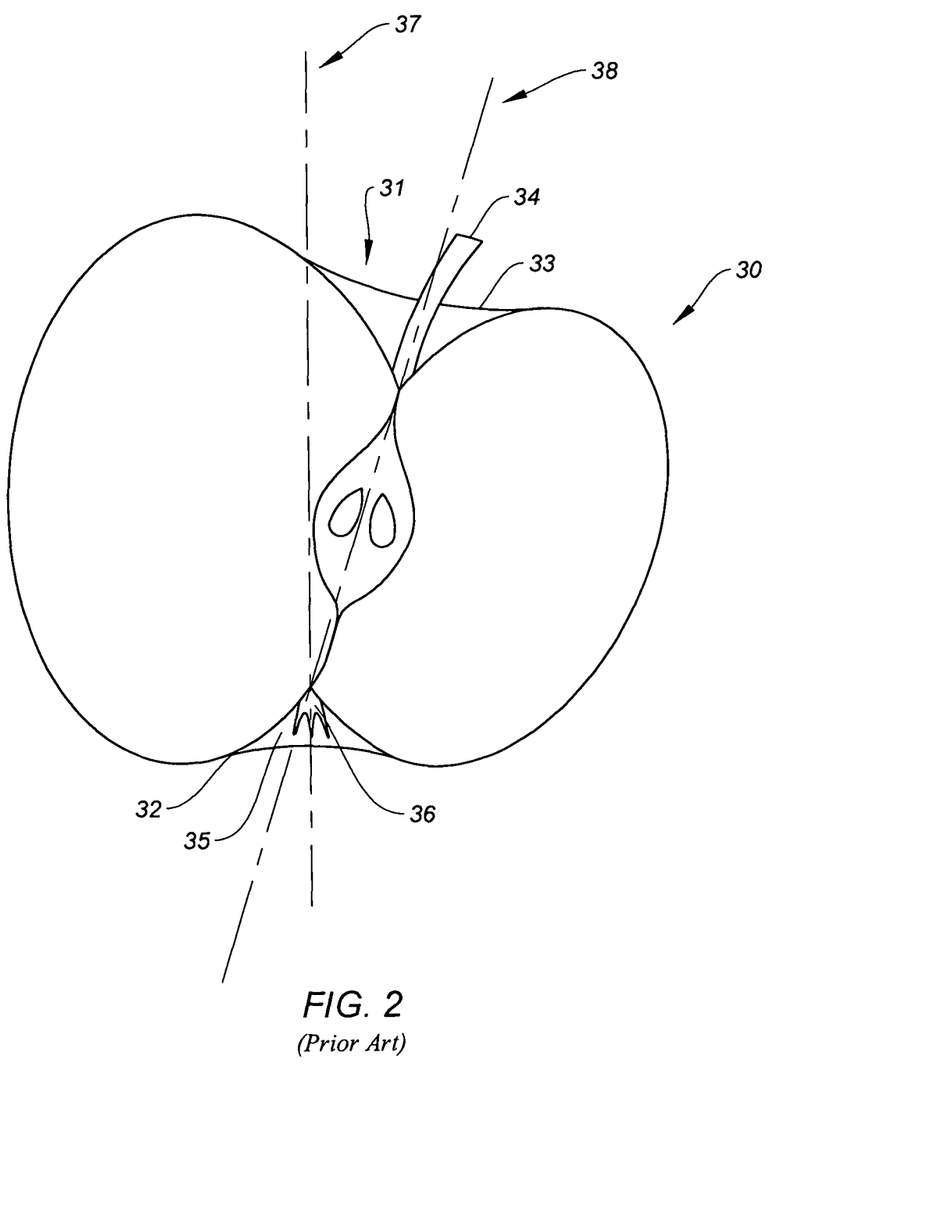
FIG. 2 is a schematic cross-sectional illustration of an unsymmetrical apple having a "dropped shoulder;"

FIG. 2 is a schematic cross-sectional representation of asymmetric apple 30, since apple 30 is not symmetric relative to axis 38, which extends through stem 34 and blossom 36. The stem indent 33 is positioned in "dropped shoulder" 31. When apple 30 enters a prior art orientor, the relatively flat blossom end 32 with indent 35 is positioned as shown in FIG. 2. The prior art orientors locate indent 35 and align apple 30 as shown in FIG. 2, with vertical axis 37 not extending through stem 34 and seed cell 39. A coring machine removes a cylindrical core along axis 37, but misses the seed cell 39 entirely. This problem is overcome by the present invention.

Figure 3:
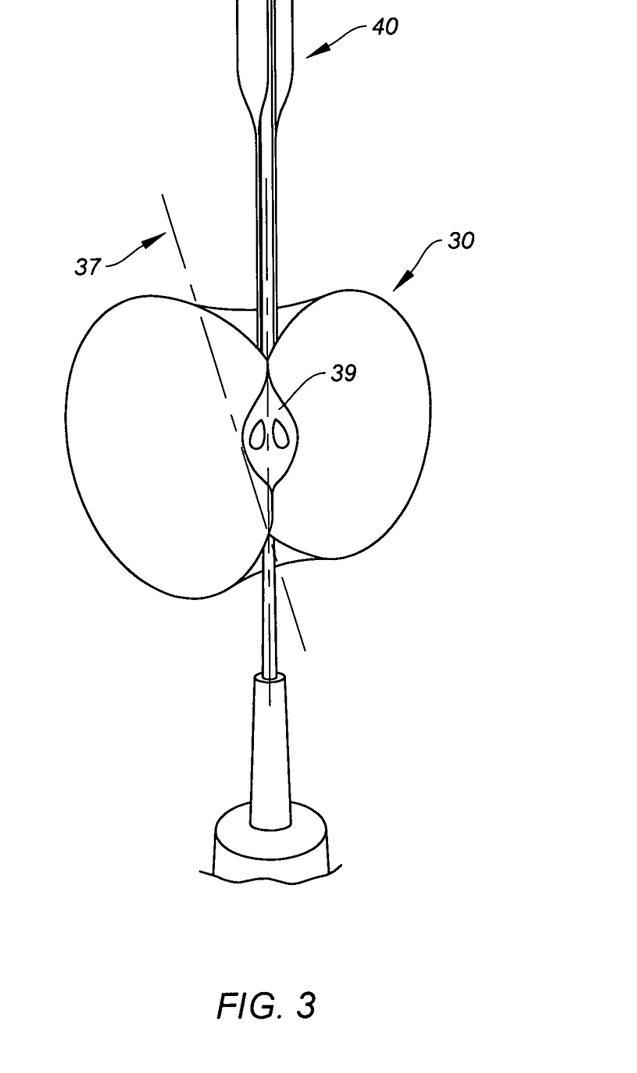
FIG. 3 is a schematic cross-sectional illustration of an asymmetrical apple having a "dropped shoulder" as properly oriented by the present invention.

FIG. 3 is an illustration of the asymmetric apple 30 of FIG. 2 properly oriented by the invention and positioned in a vertical coring device 40.

Figure 4A:
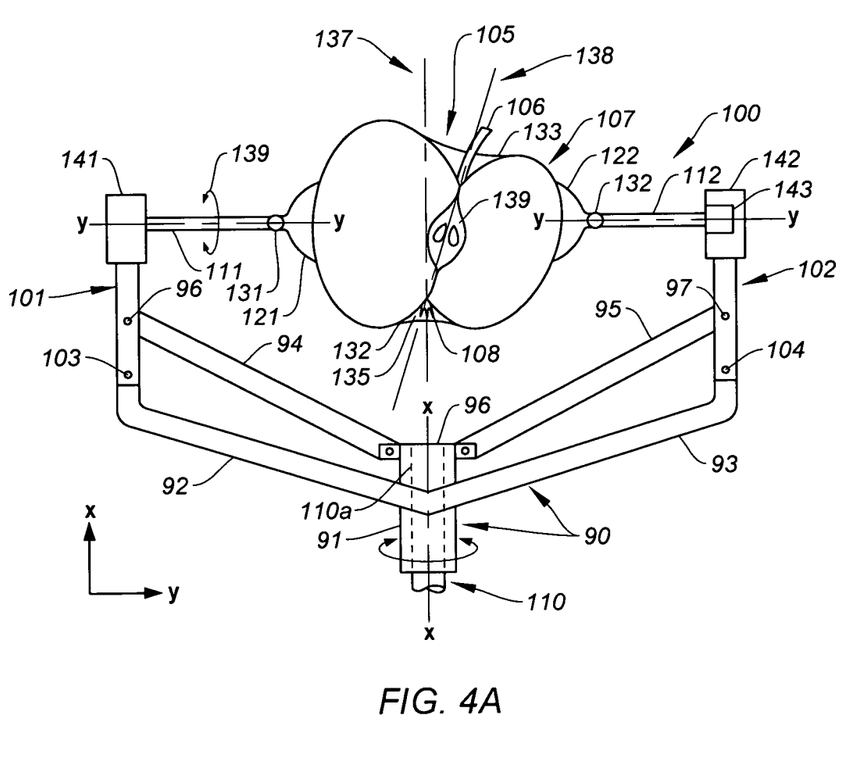
FIG. 4A illustrates an asymmetric apple having a "dropped shoulder" as presented to a manipulator.
Figure 4B:
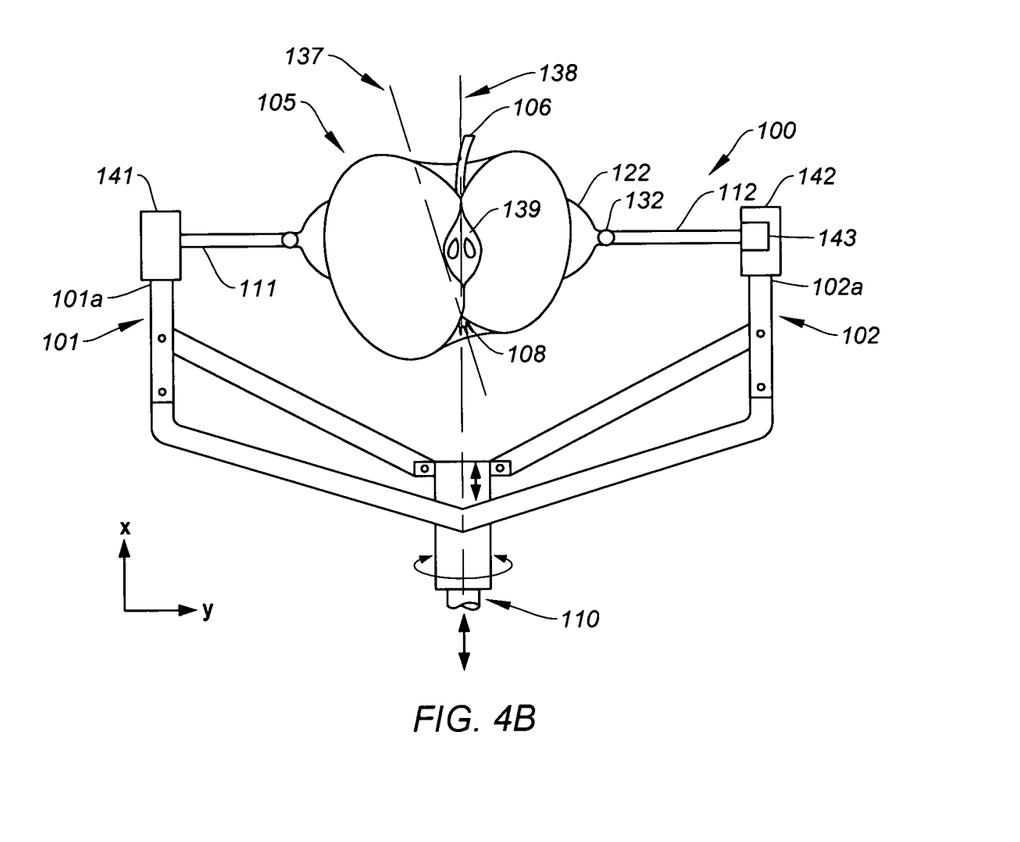
FIG. 4B illustrates the apple of FIG. 4A as properly oriented in accordance with the invention.

FIGS. 4A-4B are schematic diagrams of the concept of the invention. Current feed and singulation equipment (not shown) is used to automatically transport individual produce items such as apple 105 into programmable manipulator 100 as shown in FIG. 4A. The manipulator 100 will grab hold of the apple 105 regardless of orientation and present it to a depth imaging camera, preferably an RGB-D camera 200. The RGB-D camera 200 images each produce item such as apple 105 repeatedly as the produce item is manipulated and collects color information (Red, Green, and Blue) for every point on the surface of apple 105 as well as distance of each point from the camera. The manipulator will automatically follow a preset and programmable pattern to manipulate apple 105 to present the entire surface of the apple 105 to the camera 200. The manipulator's position is tracked using known encoders (not shown).

As shown in FIG. 4A, apple 105 has a dropped shoulder 107 and is asymmetric about an axis between its stem 106 and blossom 108. The apple core 139 is shown between stem 106 and blossom 108. Axis 138, extending from stem 106 to blossom 108, is the proper axis to be oriented vertically for transfer to coring and other processing equipment, as noted above. Axis 137 represents an axis incorrectly located by typical prior art orientors described above. Stem indent 133 includes stem 106. Blossom 108 is located in blossom indent 135. The bottom 132 of apple 105 is relatively flat.

Manipulator 100 has a generally Y-shaped base 90 which includes a support sleeve 91 which rotates about axis x-x as support shaft 110 is rotated. Support shaft is actuated by pneumatic drive means not shown. Sleeve 91 is formed integrally with and carries shoulders 92 and 93, which in turn pivotally carry arms 101 and 102, at pins 103 and 104. Support shaft 110 also is connected to, carries and actuates a four bar linkage system including pivotable arms 101 and 102 and linkage arms 94 and 95. Linkage arms 94 and 95 are pivotally connected to arms 101 and 102 by pins 96 and 97 and carried by linkage support base 96, which in turn is carried by the upper end 110a of shaft 110 (shown in phantom). As shaft 110 is advanced upwardly in FIG. 4A by pneumatic or other means, the four base linkage system causes arms 101 and 102 to separate, spreading cups 121 and 122 apart. As shaft 110 is retracted downwardly, preferably by pneumatic action, the four bar linkage causes arms 101 and 102 to move closer together to cause support cups 121, 122 to contact the apple 105 without crushing it. As shaft 110 rotates around axis x-x, the entire manipulator 100 and apple 105 are rotated in unison. The rotation of shaft 110 about axis x-x and the rotation of shafts 111 and 112 about axis y-y enable manipulator 100 to present the entire surface of apple 105 to camera 200. Swivel joints 131 and 132 are carried by shafts 111 and 112. Swivel joints carry support cups 121 and 122. Shaft supports 141 and 142 are carried at the ends of arms 101 and 102, and support shafts 121 and 122. One small servo motor 143 is carried by shaft support 142. Servo motor 143 drives both shafts 111 and 112, since shafts 111 and 112 are only rotated together when an apple is carried by manipulator 100.

Once the stem 106 and blossom 108 have been located as described above, the manipulator 100 is actuated to orient the stem 106 vertically with respect to blossom 108.

FIG. 4B illustrates proper orientation of stem 106 vertically aligned with blossom 108. It is to be understood that the apple 105 may be properly oriented with the stem 106 either vertically above blossom 108 as shown in FIG. 4B, or stem 106 may be vertically below blossom 108.

To orient apple 105 from the position shown in FIG. 4A to its proper orientation shown in FIG. 4B, manipulator 100 is rotated about the x-x axis until stem 106 and blossom 108 lie in a plane including the x axis and the z axis (shown best in FIG. 5), wherein the z axis is perpendicular to the plane including the x and y axis. Once the stem 106 and blossom 108 lie in the plane including the x and z axes, cups 121 and 122 are rotated around the y-y axis to reach the proper orientation shown in FIG. 4B. Once the proper orientation is achieved, cups 121 and 122 are separated by support shaft 110 moving upwardly in FIG. 4B by a pneumatic drive (not shown) to release the oriented apple to known transfer apparatus for further processing.

It is to be understood that in FIGS. 4A and 4B, camera 200 and manipulator 100 are connected to a computer not shown for clarity. The drive mechanism for manipulator 100 is also not shown for clarity.

In a first embodiment of the invention, images from camera 200 are used to create a 3D model of the surface of apple 105. This 3D model is a "Digital three dimensional characterization" of the surface of the produce item, apple 105, being manipulated. An Iterative Closest Point (ICP) algorithm is used to compare the generated model with a previously created pre-existing digital library of a plurality of 3D models of properly oriented symmetric and asymmetrical apples (or other produce items) to locate the closest match between the current generated model and the digitally stored models. The motions needed to correct the orientation of the apple from its current state to a preferred state are calculated. Those motions are then carried out by the manipulator 100 to produce a properly oriented apple as shown in FIG. 4B. The Iterative Closest Point (ICP) algorithm is known in the art and readily available.

Figure 5:
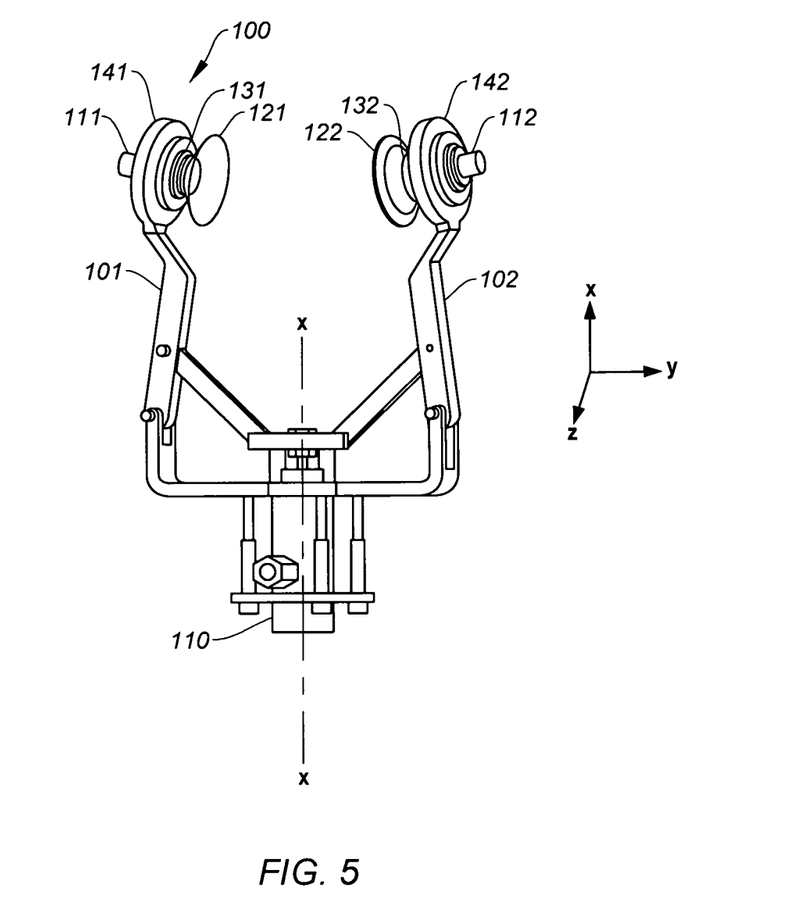
FIG. 5 is a more detailed, perspective view of the manipulator shown in FIGS. 4A and 4B with a modification in the swivel joint supports.

FIG. 5 is a perspective and more detailed view of preferred manipulator 100 shown in FIGS. 4A and 4B, in which shafts 111, 112 shown in FIGS. 4A and 4B have been shortened, so that swivel joints 131 and 132 are carried by shaft supports 141 and 142. As noted above one small servo motor 143 (FIG. 4A) is carried by shaft support 142 and is not visible in FIG. 5. As noted above, manipulator 100 has arms 101 and 102 carried by shaft 110 which rotates about axis x-x. Support cups 121 and 122 are carried by swivel joints 131, 132 carried by shafts 111 and 112. Support cups 121, 122 are utilized to contact and manipulate apple 105 to achieve correct orientation.

Figure 6:
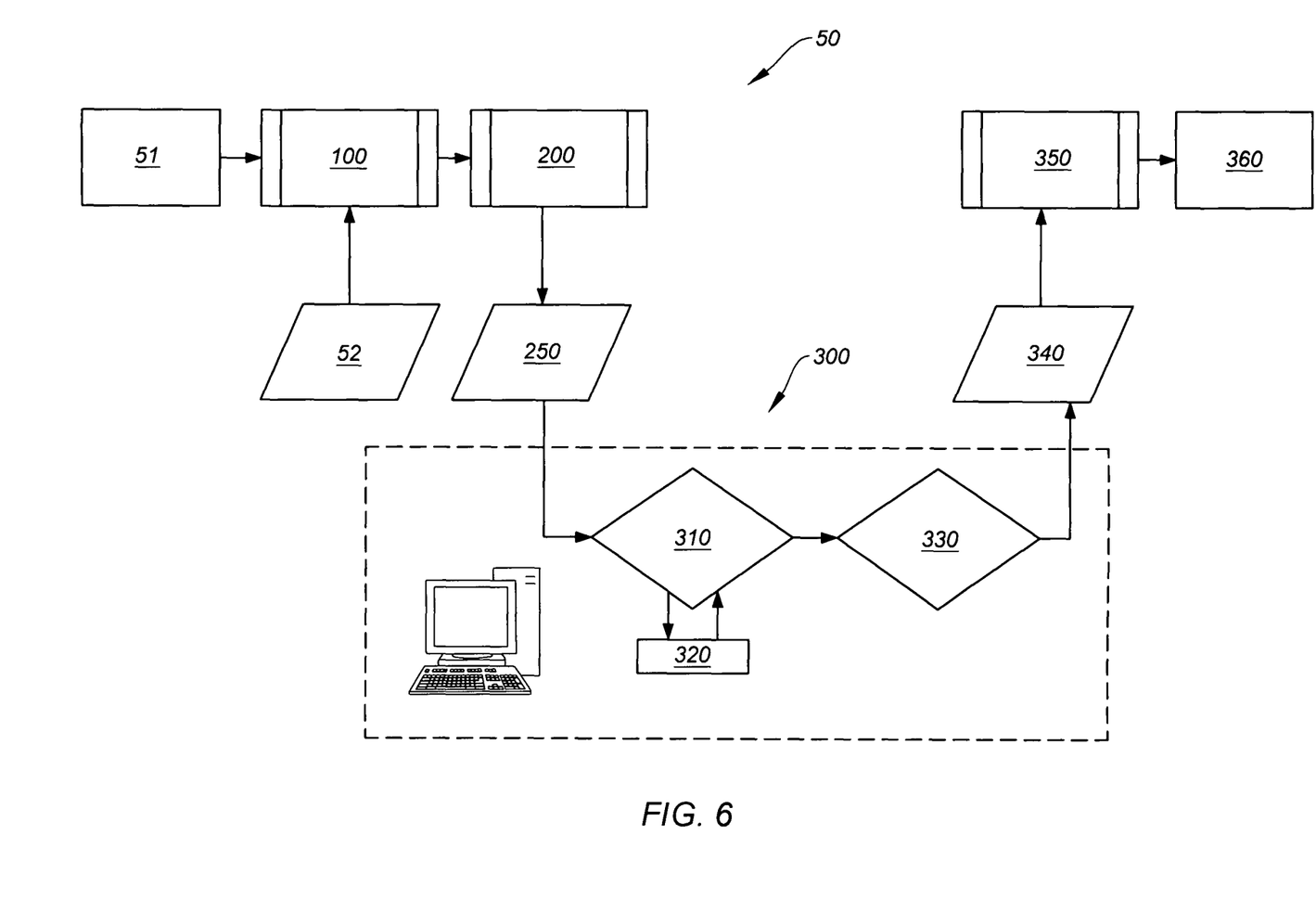
FIG. 6 is a block diagram of the control system of a first embodiment of the invention.

FIG. 6 is a block diagram of the control system for said first embodiment is shown generally as 50. A known feed system 51 is actuated to transport an apple to the manipulator 100. The manipulator 100 is actuated to rotate the apple in a preprogrammed sequence stored at 52. One or more depth imaging cameras 200 is actuated to scan the apple repeatedly as it is rotated by manipulator 100.

The three dimensional model 250 of the current apple being scanned is fed into computer 300. An Iterative Closest Point (ICP) algorithm 260 is used to compare the model 250 with a digital library 320 of three dimensional digital models of properly oriented symmetrical and asymmetrical apples to determine the closest match and the proper pose for the current apple. The manipulator motions to properly orient the current apple are calculated at 330 and fed to the manipulator at 340. The manipulator is actuated at 350 to properly orient the current apple, and the apple is then transferred to coring or peeling at 360.

Figure 7A:
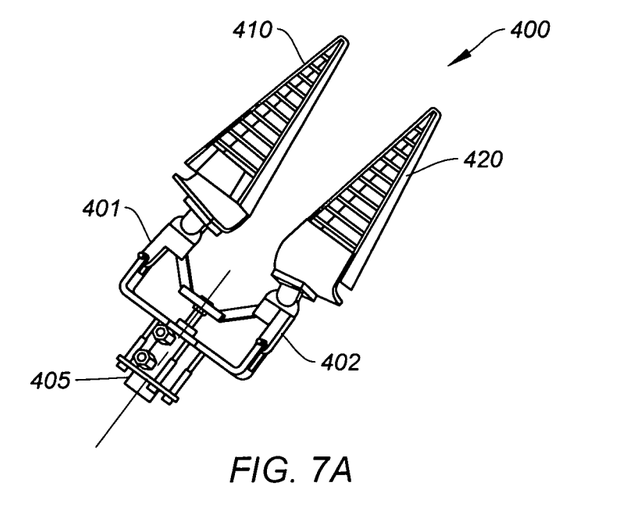
FIGS. 7A and 7B are perspective views of an alternate manipulator.
Figure 7B:
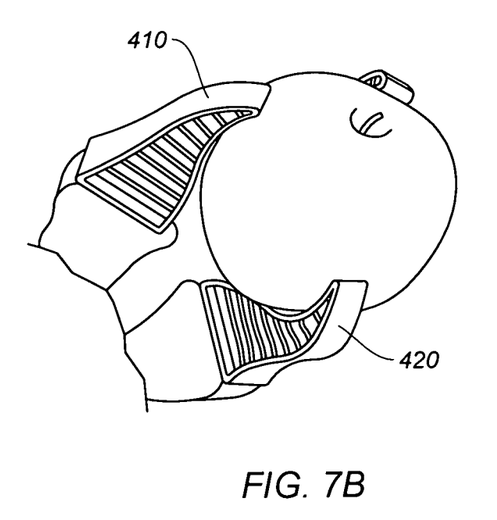

FIGS. 7A and 7B show an alternative manipulator 400 that grips the apple using the fin ray effect. Fins 410 and 420 are carried by arms 401 and 402, which in turn are carried by a support shaft 405 which rotates about axis x-x, in similar fashion to manipulator 100 shown in FIGS. 4A, 4B and 5. The fins 410 and 420 grip the produce as shown in FIG. 7B, as known in the manipulator art.

Figure 8:
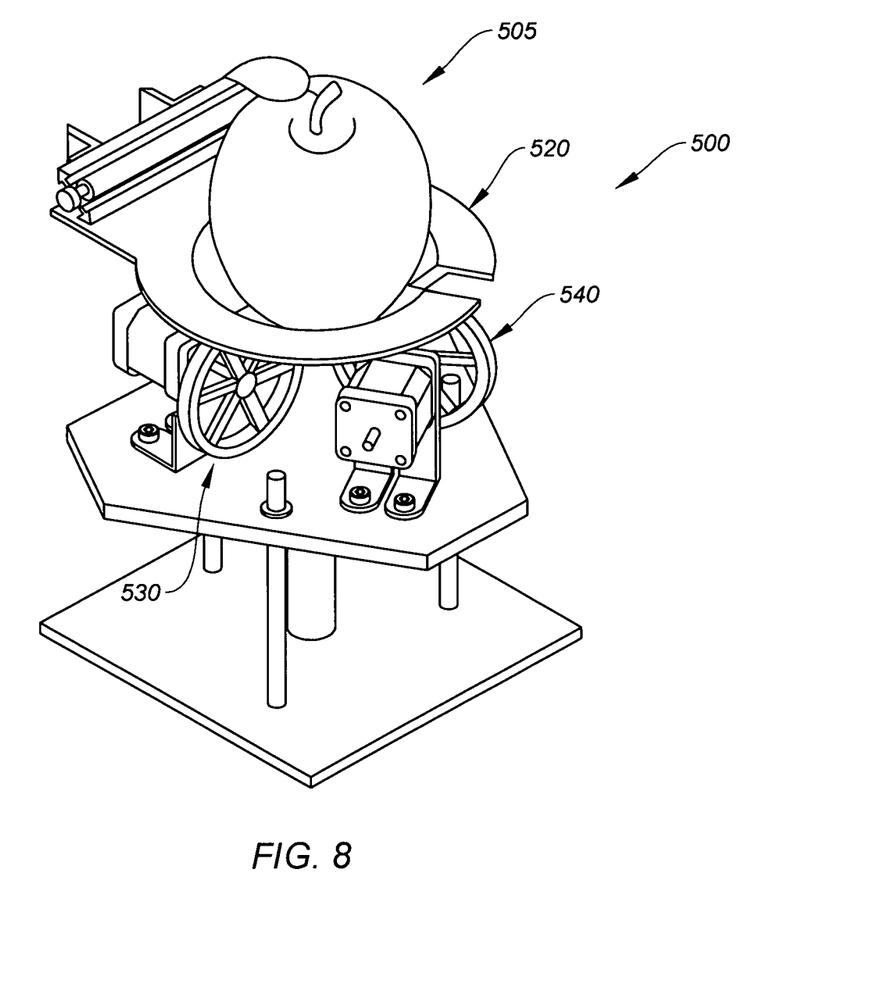
FIG. 8 is a perspective view of a further alternate manipulator.

FIG. 8 shows a further manipulator 500 based on an orienting cup 520 with 2 wheels 530, 540 off center rather than one rotating wheel in the center. Orienting cup 520 has an opening (not visible in FIG. 8) formed in its bottom, as known in the art. Apple 505 is rotated by off-center wheels 530 and 540 so that the entire surface of apple 505 can be repeatedly imaged by one or more depth imaging cameras (not shown in FIG. 8). When the entire surface of apple 505 has been imaged, either or both wheels 530, 540 are actuated to properly orient apple 505.

Figure 9:
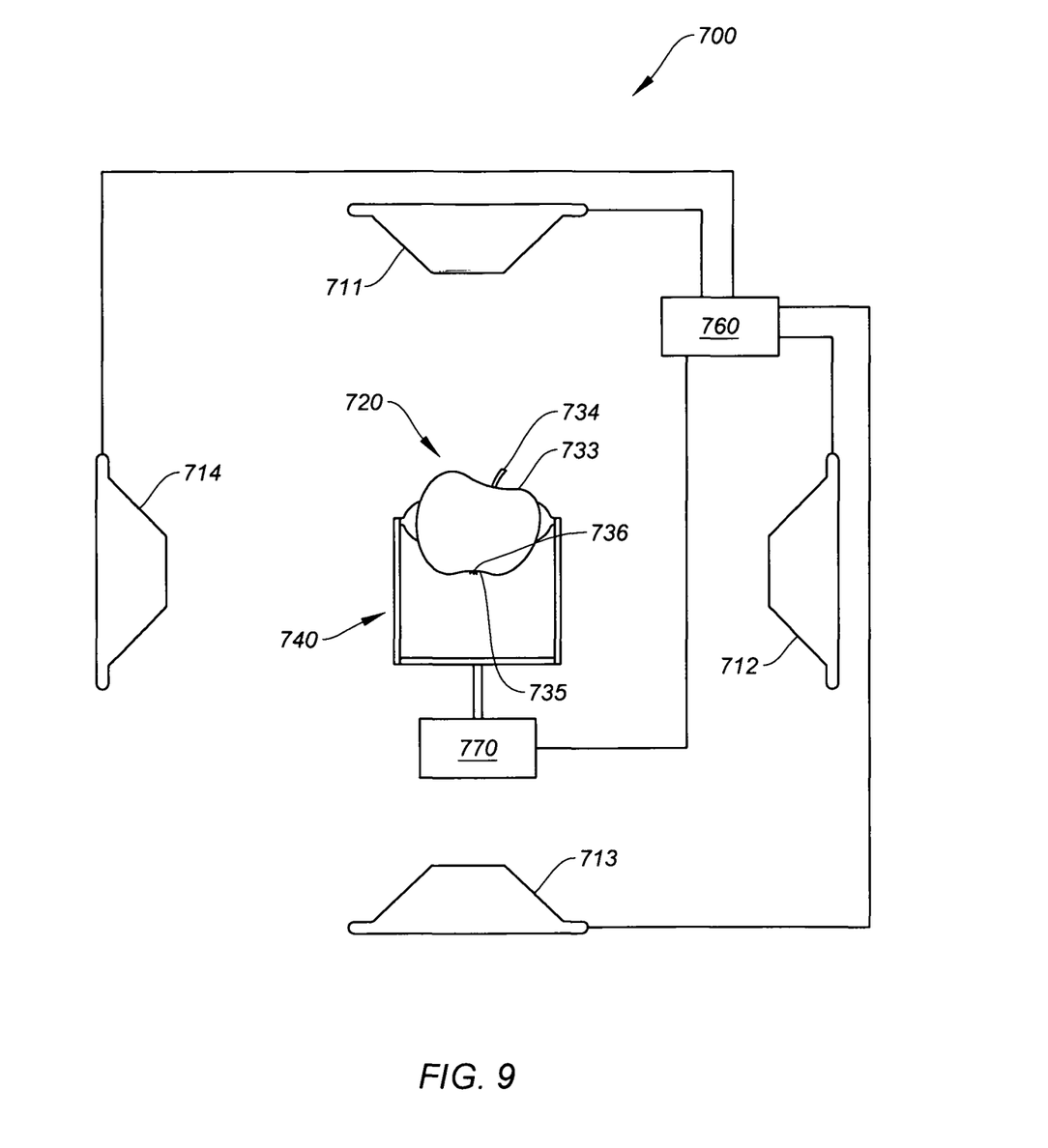
FIG. 9 is a schematic representation of a second embodiment of the invention.
Figure 10:
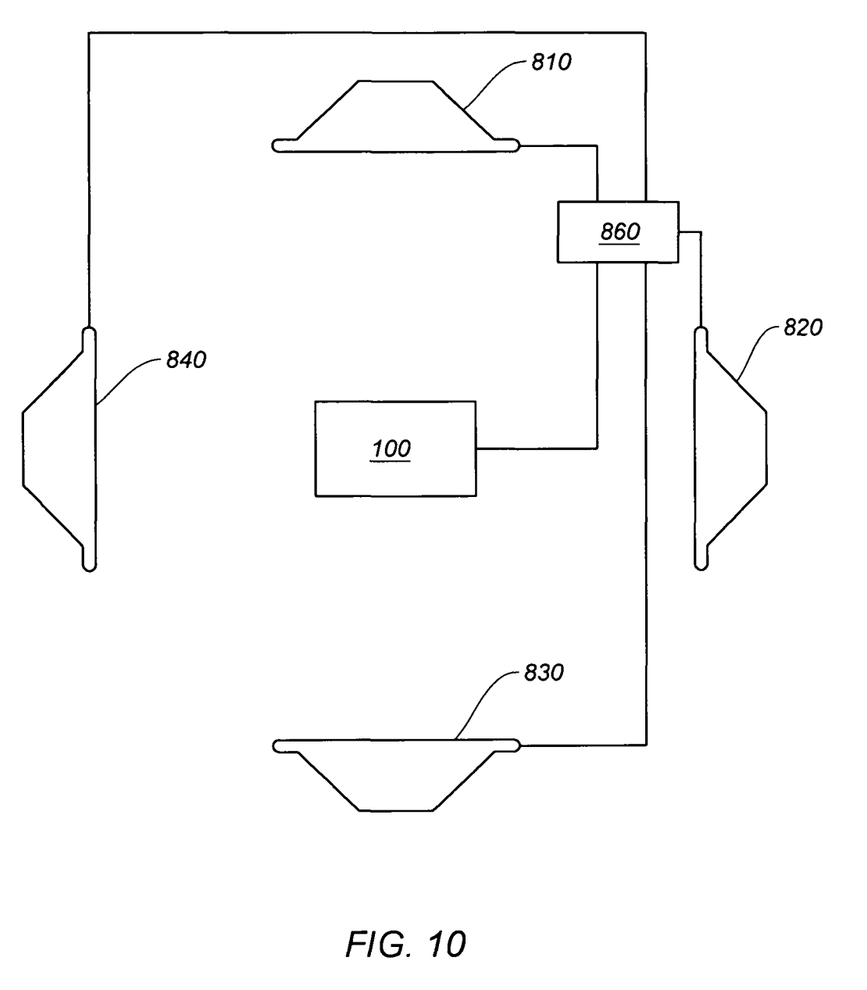
FIG. 10 illustrates the preferred use of 4 depth imaging cameras.

FIG. 9 is a schematic diagram representing a second embodiment of the invention shown generally as 700. Four depth imaging cameras 711-714 are spaced around manipulator 740 and are repeatedly imaging an asymmetric apple 720 having a stem 734 in stem indent 733 and a blossom 736 in blossom indent 735 as apple 720 is being manipulated. As the apple 720 is manipulated by manipulator 740 (such as manipulator 100 shown and described above the indents) 733 and 736 are presented to cameras 711-714 along with the entire surface of apple 720. As the apple continues to be rotated, a three dimensional image of the surface of apple 720 is fed by cameras 711-714 to computer 760. Computer 760 is connected to the drive 770 for manipulator 740. Computer 760 utilizes the known Principal Axis of Curvature (PAC) algorithm to create a three dimensional map of the slope for each point on the surface of apple 720. The stem indent 733 and blossom indent 735 have the highest clusters of high slopes, which clusters are utilized to locate the indents. When the indents are located, the location of stem 734 and blossom 736 are known and the manipulator 740 is actuated by computer 760 to properly orient the apple 720 for processing as described above. Normal orientation for apples aligns stem 734 vertically with blossom 736, with either the stem being above or below the blossom. In using the PAC algorithm, no digital library is required. Although 4 depth imaging cameras are shown in FIG. 10, acceptable results can be achieved with a single camera. A block diagram of the control system for this embodiment is the same as the diagram of FIG. 6, except that the 3D image at 250 is of the slopes for each point on the surface of the apple, the algorithm at 310 is the PAC rather than ICP, and the digital library shown at 320 is not used with the PAC algorithm.

The Principal Axis of Curvature (PAC) algorithm is known and is not described in detail here. The basic two steps of the PAC algorithm are:

1. Represent the segmented apple point cloud in terms of curvature by multiplying surface normal by curvature magnitude. The result is a point cloud that represents the magnitude of surface changes vs. direction. This translates the higher curvature around the stem and blossom indents into a point cloud that is elongated along the stem-blossom axis.

2. Estimate the principal axis of the curvature representation of the apple using a robust version of PCA. The principal axis is the axis of maximum variability. The principal axis, or first principal component, represents the estimated axis of the apple. Perform a few iterations of principal axis estimation with outlier removal.

As shown in the diagram of FIG. 10, the most preferred embodiment of the invention utilizes four RGB-D cameras 810, 820, 830 and 840 placed around manipulator 100, shown in FIGS. 4A, 4B and 5. Computer 860 is connected to manipulator 100 and all four cameras 810, 820, 830 and 840.

One or more depth imaging cameras may be utilized. The RGB-D cameras are preferred, since they also provide color information. The color information is utilized to detect dark or discolored regions on the surface of bruised apples which are not appropriate for automatic coring or peeling. Such bruised apples are separated and either discarded or processed by alternate means.

As used herein and in the claims, the phrase "digital three dimensional characterization of the surface" refers to any useful digital depiction, model or representation of the shape of the surface or of any characteristic of the surface such as slope.

As used herein and in the claims, the phrase "depth imaging camera" refers to any camera capable of generating three dimensional images or characterizations of the surface of an object within the view of said camera.

It is to be understood that locating the stem and blossom is done in most instances in the case of apples by locating the stem indent and/or blossom indent using the PCA algorithm and assuming that the stem and blossom are located at the center of each respective indent. Accordingly, as used herein and in the claims, the phrase "locating the stem and blossom" is used broadly to include locating the stem indent and blossom indent. In addition, for many varieties of peaches, pears and apricots where the stem and/or blossom indents may be too small to use the PCA algorithm, the first embodiment using a digital library and the ICP algorithm would be the appropriate method.

In the case of peaches and apricots, the proper orientation is required for removing the stone or pit. The present invention may be utilized to locate not only the stems and blossoms of peaches and apricots, but also the "suture line" of these items. Proper orientation of the suture line is significant in removing the stone or pit, as is known in the art.

The foregoing description of the invention has been presented for purposes of illustration and description and is not intended to be exhaustive or to limit the invention to the precise form disclosed. Modifications and variations are possible in light of the above teaching. The embodiments were chosen and described to best explain the principles of the invention and its practical application to thereby enable others skilled in the art to best use the invention in various embodiments suited to the particular use contemplated.

We claim:

1. A method of automatically orienting produce items, wherein each produce item has a stem and a blossom comprising the steps:

transporting individual produce items into a programmable manipulator, manipulating each produce item, imaging each produce item repeatedly with one or more depth imaging cameras as said produce item is manipulated, creating a digital three dimensional characterization of the surface of said produce item being manipulated, utilizing said digital three dimensional characterization of the surface of said produce item being manipulated to locate said stem and said blossom in three-dimensional space using a principal axis of curvature algorithm, and correcting the orientation of said produce item to a proper orientation by:

rotating said produce item about a first pre-determined axis until said stem and said blossom lie in a first pre-determined plane; and rotating said produce item about a second pre-determined axis until said stem and said blossom lie along a pre-determined line.

2. The method of claim 1 wherein said produce item is an apple having a stem indent in which said stem is located and a blossom indent in which said blossom is located and wherein the principal axis of curvature algorithm is utilized to locate said stem indent and said blossom indent.

3. The method of claim 1 wherein said digital three dimensional characterization is a three dimensional model of the surface of said produce item being manipulated, wherein a plurality of three dimensional models of properly oriented produce items is stored in a digital library, and wherein an iterative closest point algorithm is utilized to compare said generated three dimensional model with said stored three dimensional models of properly oriented produce items and to cause a programmable manipulator to correct the orientation of the produce based on the comparison.

4. The method of claim 1 wherein said manipulator grips said produce item using the fin ray effect.

5. The method of claim 1 wherein said manipulator utilizes an orienting cup with two off-center drive wheels beneath said orienting cup to cause said produce item to rotate to present the entire surface of said produce item to said depth imaging camera.

6. The method of claim 1 wherein said depth imaging camera is an RGB-D camera.

7. The method of claim 1 wherein two or more depth imaging cameras are utilized to image said produce item being manipulated.

8. The method of claim 1 wherein four RGB-D cameras are positioned around said produce item being manipulated, and each camera generates a three dimensional model of the produce item being manipulated.

9. The method of claim 1 where said manipulator follows a preset motion pattern to present the entire surface of the produce item to the camera.

10. The method of claim 1 wherein a position of said manipulator is tracked using encoders.

11. The method of claim 1 wherein said produce items are apples.

12. The method of claim 1 wherein one or more RGB-D cameras are utilized to detect the color of any bruises to said produce items that require that produce item to be either separated for special processing or to be discarded.

13. A method of automatically orienting produce items, wherein each produce item has a stem and a blossom comprising the steps:

imaging a produce item repeatedly with one or more depth imaging cameras as said produce item is manipulated to create a three dimensional characterization of said produce item, comparing, using an iterative closest point algorithm, the created digital three dimensional characterization of the surface of said produce with a digital library of a plurality of three dimensional models of properly oriented and symmetric produce items to locate a closest match between the created digital three dimensional characterization of the surface of said produce and one of three dimensional models in the digital library, and correcting the orientation of said produce item to a proper orientation based on the located closest match by:
  rotating said produce item about a first pre-determined axis until said stem and said blossom lie in a first pre-determined plane; and
  rotating said produce item about a second pre-determined axis until said stem and said blossom lie along a pre-determined line.

14. The method of claim 13, further comprising:
transporting individual produce items into a programmable manipulator,
manipulating each produce item, and
actuating said manipulator to correct the orientation of said produce item to said proper orientation.

15. The method of claim 14 wherein said correcting uses said manipulator to grip said produce item using the fin ray effect.

16. The method of claim 14 wherein said correcting uses said manipulator that comprises an orienting cup with two off-center drive wheels beneath said orienting cup to cause said produce item to rotate to present the entire surface of said produce item to said depth imaging camera.

17. A system of automatically orienting produce items, wherein each produce item has a stem and a blossom comprising:
  a manipulator to transport individual produce items and manipulate each produce item,
  an imager to image each produce item repeatedly with one or more depth imaging cameras as said produce item is manipulated,
  a data processor to create a digital three dimensional characterization of the surface of said produce item being manipulated and utilize said digital three dimensional characterization of the surface of said produce item being manipulated to locate said stem and said blossom in three-dimensional space using a principal axis of curvature algorithm, and
  wherein said manipulator is configured to correct the orientation of said produce item to a proper orientation by:
    rotating said produce item about a first pre-determined axis until said stem and said blossom lie in a first pre-determined plane; and
    rotating said produce item about a second pre-determined axis until said stem and said blossom lie along a pre-determined line.

* * * * *